US00PP24440P3

(12) United States Plant Patent
Leis et al.

(10) Patent No.: US PP24,440 P3
(45) Date of Patent: May 13, 2014

(54) STRAWBERRY PLANT NAMED 'LINOSA'

(50) Latin Name: *Fragaria L.*
Varietal Denomination: LINOSA

(75) Inventors: Michelangelo Leis, Ferrara (IT); Alessio Martinelli, Ferrara (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Societá Consortile A R.L., Comacchio FE (IT)

( * ) Notice: Subject to any disclaimer, the term of this patent is extended or adjusted under 35 U.S.C. 154(b) by 0 days.

(21) Appl. No.: 13/385,298

(22) Filed: Feb. 13, 2012

(65) Prior Publication Data

US 2012/0246769 P1 Sep. 27, 2012

(30) Foreign Application Priority Data

Feb. 14, 2011 (QZ) ..... PBR 20110359

(51) Int. Cl.
*A01H 5/00* (2006.01)

(52) U.S. Cl.
USPC ..... Plt./209

(58) Field of Classification Search
USPC ..... Plt./209, 208
See application file for complete search history.

*Primary Examiner* — Kent L Bell
(74) *Attorney, Agent, or Firm* — Foley & Lardner LLP

(57) ABSTRACT

A new and distinct variety of *Fragaria L.* named 'LINOSA', characterized by the description herein.

4 Drawing Sheets

Latin name of the genus and species claimed: *Fragaria L.*
Variety denomination: 'LINOSA'.

PRIORITY CLAIM

This application claims the benefit of European Community Plant Variety Office Plant Breeders' Rights Application No. 2011/0359, filed Feb. 14, 2011.

BACKGROUND OF THE INVENTION

The present invention relates to a new and distinct strawberry variety named 'LINOSA', which was the result of a controlled cross between the strawberry variety 'CIVRI30' (Breeder reference, unpatented) and a not released selection of Consorzio Italiano Vivaisti named 'R6R7-19'.

The progeny was first asexually propagated by stolons in S. Giuseppe di Comacchio Ferrara, Italy, in 2005.

The 'LINOSA' variety was tested over the next several years in different European areas with continental climates. The tests started in 2006 and continued until 2010.

BRIEF SUMMARY OF THE INVENTION

Plants of the new Strawberry variety 'LINOSA' can be distinguished from plants of the Strawberry variety 'CIVRI30' by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| 'CIVRI30' | Fruit Size<br>Insertion of Achenes | Medium to Large<br>Level with Surface | Large to Very Large<br>Below surface |

Plants of the new Strawberry variety 'LINOSA' can be distinguished from plants of the Strawberry variety 'R6R7-19' by the following unique combination of characteristics described in Table 2:

TABLE 2

| Comparison with parent variety: | | | |
|---|---|---|---|
| Denomination of similar variety | Characteristic in which the similar variety is different | State of expression of similar variety | State of expression of candidate variety |
| 'R6R7-19' | Leaf: upper side color<br>Plant vigor<br>Color of mature fruit | RHS 131A<br>Weak<br>RHS 46A | RHS 139A<br>Medium<br>RHS 46B |

Asexual reproduction of this new variety by stolons shows that the foregoing and all other characteristics and distinctions come true to form and are established and transmitted through succeeding propagations. The new variety reproduces true to type.

BRIEF DESCRIPTION OF THE PHOTOGRAPHS

The accompanying photographs illustrate the overall appearance of the new Strawberry 'LINOSA' showing the colors as true as is reasonably possible with colored reproductions of this type. Colors in the photographs may differ slightly from the color value cited in the detailed botanical description, which accurately describe the color of 'LINOSA'.

Figure 1:
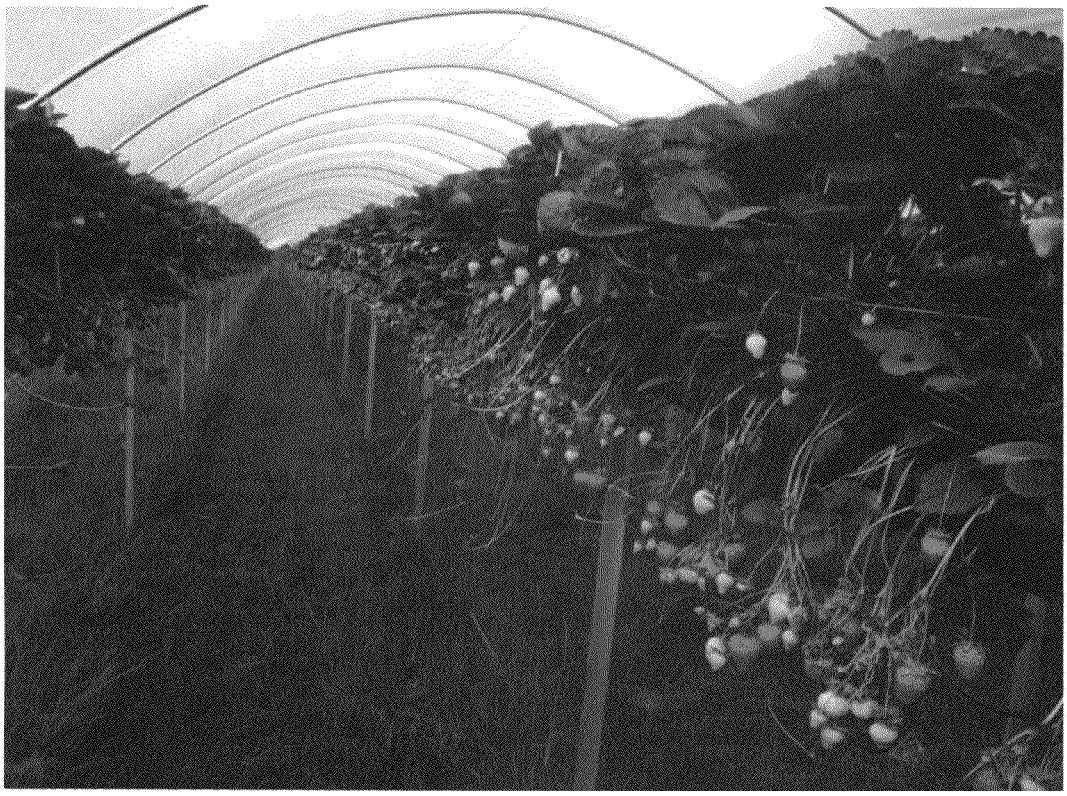
FIG. 1 shows the plant of 'LINOSA'.
Figure 2:
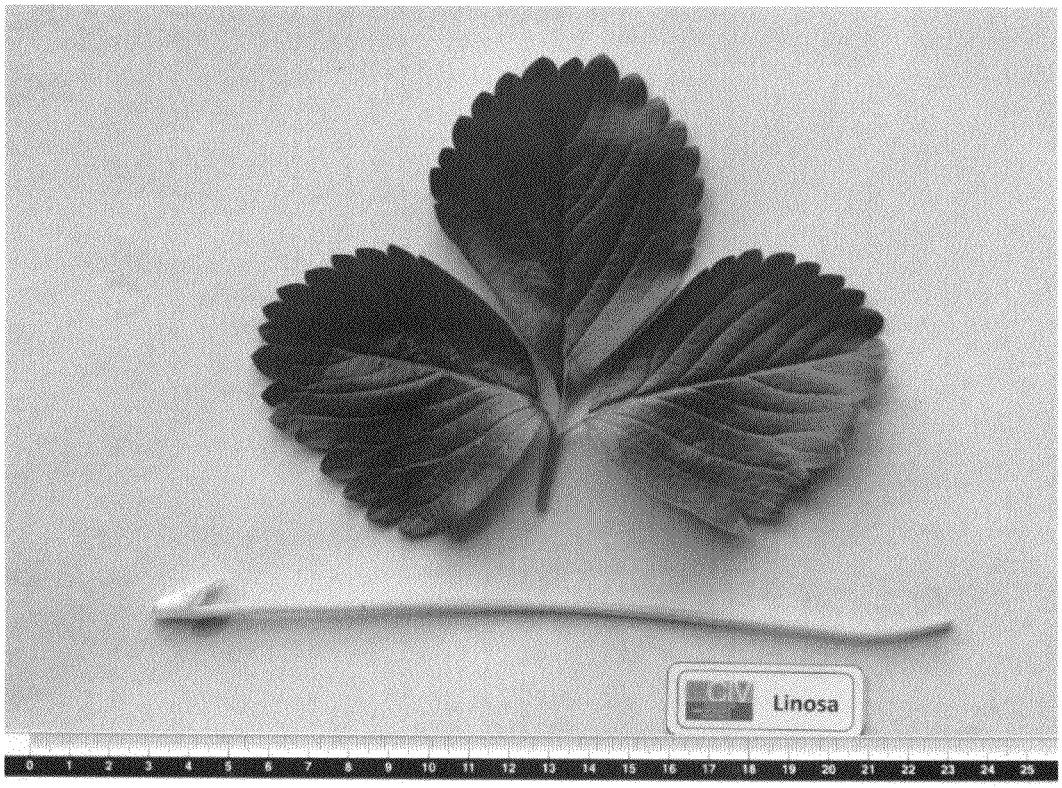
FIG. 2 shows the leaves of 'LINOSA'.
Figure 3:
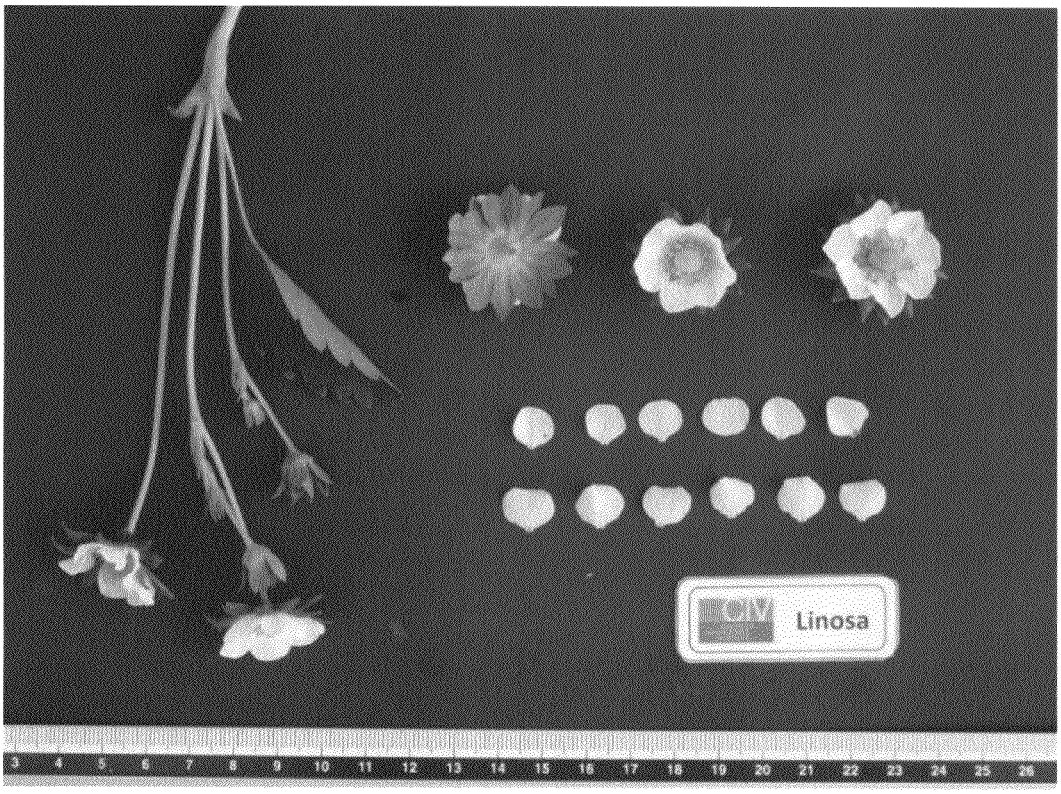
FIG. 3 shows the flowers of 'LINOSA'.
Figure 4:
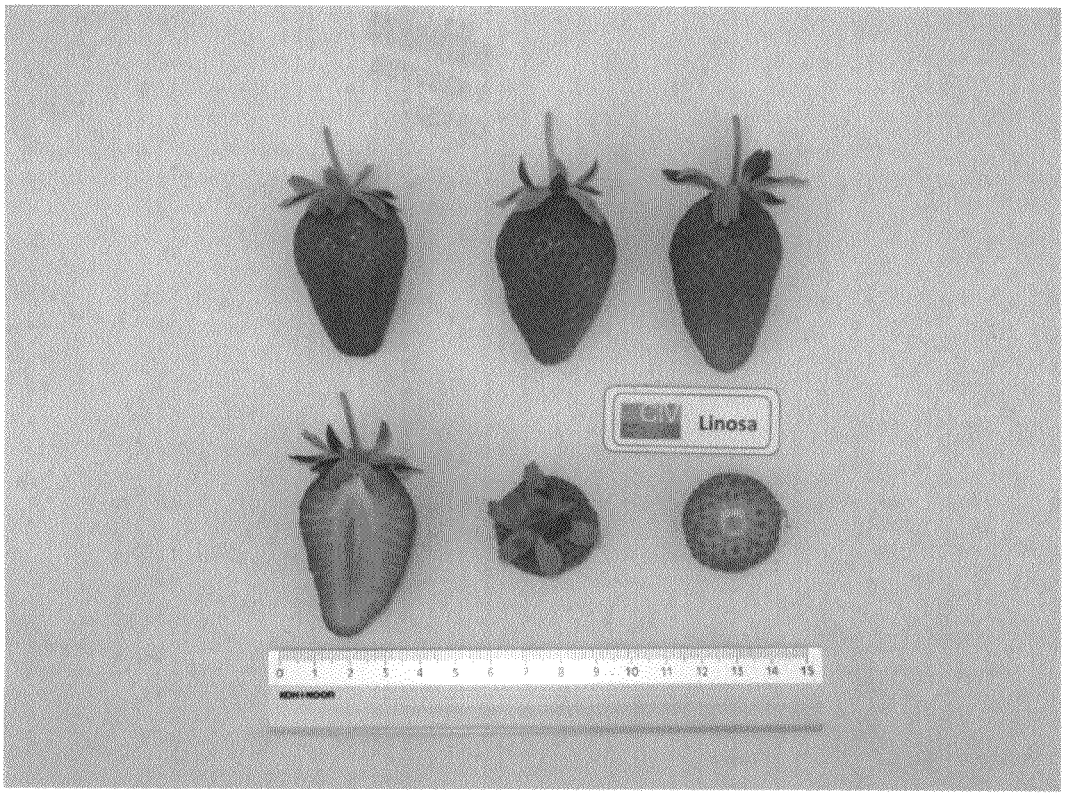
FIG. 4 shows the fruits of 'LINOSA'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'LINOSA' variety, unless otherwise noted, is based on observations taken of plants and fruits, and asexually reproduced progeny, grown at S. Giuseppe di Comacchio, Ferrara, Italy.

The observed plants were one year old plants. The plants used in the production field are produced in a nursery in S. Giuseppe di Comacchio, dug in December, cold stored, and planted in production fields in the middle of April.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Color Chart.

Plant:

*Habit.*—Semi-upright.

*Density.*—Medium.

*Vigor.*—Medium.

*Overall shape.*—Slightly upright.

*Height.*—0.26-0.28 meters.

*Width.*—0.35-0.40 meters.

Leaf:

*Color of upper side.*—RHS 139A green group; color of under side: RHS 138B green group.

*Size of leaf.*—Medium.

*Length.*—About 12.5 cm.

*Width.*—About 14 cm.

*Leaf surface ondulation or blistering.*—Medium.

*Leaf arrangement.*—Slightly overlapping.

*Leaf glossiness.*—Medium.

*Number of leaflets.*—Three only.

*Petiole characteristics.*—Length: About 15-16 cm. Diameter: 2.85 mm. Texture: hairy. Pubescence: Medium. Position of hairs: horizontal. Color: RHS 145A yellow-green group.

*Stipule.*—Length: 3.2 cm. Width: 1.3 cm. Pubescence: Weak. Color: RHS 144D, green group. Anthocyanin coloration: absent.

*Terminal leaflet.*—Length/width ratio: Equal. Length: About 7.5 to 8.5 cm. Width: About 7.5 to 8.5 cm. Shape of Terminal Leaflet: Rounded. Shape of Base: Obtuse. Shape of Apex: Rounded. Shape of Margin: Serrate to Crenate. Texture: Upper side: Medium glossiness/medium blistering. Under side: Medium vein expression. Shape in Cross Section: Concave.

*Stolons.*—Number about 6-7. Thickness: Medium, about 2.91 mm. Pubescence: Sparse. Color RHS 145A, yellow-green.

Inflorescence:

*Position relative to foliage.*—At same level or slightly above.

*Length.*—About 18 cm.

*Flower.*—Form: Rosaceae. Size: Medium. Arrangement of Petals: Overlapping. Diameter of primary flowers. About 3 cm. Diameter of secondary flowers. About 2.5 cm. Flower Depth (height of the corolla): 12 to 13 mm, measured when the flowers are fully open. Fragrance: No significant fragrance.

*Petals.*—Number of petals: Normally 6. Shape: Orbicular. Margin: Entire. Length: 9.88 mm. Width: 10.3 mm. Apex: rounded. Base: concavo-convex. Length/Width ratio: As long as broad; 0.95. Color (upper and under surface): RHS 155B, white group. Texture (upper and under surface): smooth. Time from bloom to mature fruit: About 30 to 35 days.

*Calyx.*—Diameter: average 35 mm. Size of calyx relative to corolla: larger.

*Sepal.*—Arrangement: Overlapping. Shape: Elliptical. Apex: Convex. Margin: Entire. Length: about 14 mm. Width: 6 mm. Number per flower: 16. Color of upper side: RHS 138A green group. Color of under side: RHS 139C green group. Texture (upper and under surface): hairy. Pubescence: weak.

Reproductive organs:

*Stamens.*—Numerous with pollen present, fertile and abundant. Length: approximately 2.5 mm. Color: RHS 157A, green-white.

*Anthers.*—Generally average in size. Length: About 1.3 mm. Width: About 0.9 mm. Color: RHS 14 B yellow-orange ; darkening with advanced maturity.

*Pollen.*—Fertile and abundant. Color: RHS 14 A yellow-orange.

*Pistils.*—Numerous, generally average in size. Color: RHS 151C yellow-green.

Fruit:

*Fruit truss.*—Attitude: Semi-erect.

*Ratio of length/maximum width.*—Much longer.

*Color of mature fruit.*—RHS 46B red.

*Color of flesh.*—RHS 33A orange-red, RHS 35B orange-red, and RHS 155D white.

*Length.*—50-60 mm.

*Width.*—35-45 mm.

*Calyx diameter.*—30-40 mm.

*Average weight.*—20-35 grams.

*Achene color.*—RHS 153A yellow green.

*Number of achenes per berry.*—330-390.

*Achene size.*—Length about 1.2 mm, width about 0.9 mm.

*Weight of* 1000 *achenes.*—0.40 grams.

*Peduncle length* (*of inflorescence stem*).—Primary fruit about 9-11 cm, secondary fruit about 6-7 cm.

*Peduncle color.*—RHS 138 C green group.

*Peduncle diameter.*—1.8 mm.

*Peduncle texture.*—Hairy.

*Marketable yield* (*gm/plant*).—About 800-1000 grams.

*Fruit size.*—Large.

*Predominant shape.*—Ovoid.

*Difference in shapes between primary and secondary fruit.*—Moderate.
*Band without achenes.*—Absent to very narrow.
*Unevenness of surface.*—Even or very slightly uneven.
*Evenness of color.*—Even or very slightly uneven.
*Glossiness.*—Medium.
*Insertion of achenes.*—Below surface.
*Insertion of calyx.*—Raised.
*Attitude of the calyx.*—Outwards.
*Size of calyx in relation to fruit diameter.*—Slightly smaller.
*Adherence of calyx.*—Weak.
*Firmness of flesh.*—Firm.
*Hollow center expression.*—Medium.
*Flavor.*—Good.
*Soluble solids* (% *brix*).—7.5-8.5.
*Time of first flowering.*—About 28-32 days after planting using cold stored plants quality A. Typically in S. Giuseppe di Comacchio Ferrara (Italy), planting beginning of April and first flowering beginning of May.
*Time of first harvesting.*—About 30-35 days after first flowering.
*Harvest period.*—June to November.
*Type of bearing.*—Fully remontant.

Disease resistance: The 'LINOSA' variety has been tested for several years and it has manifest a good rusticity plant, quite resistant to leaf and root diseases. With a robust and efficient root system, the plant adapts well to depleted soils and generally does not require soil disinfection. Due to its hardiness and vigor, it is well-suited to tired soil and only needs a small amount of fertilizers. Linosa shows good tolerance to *Phytophthora cactorum* and powdery mildew.

What is claimed is:

1. A new and distinct variety of *Fragaria L.* plant named 'LINOSA', as illustrated and described herein.

* * * * *